(12) United States Patent
Huang

(10) Patent No.: US 8,991,430 B2
(45) Date of Patent: Mar. 31, 2015

(54) MEDICAL VALVE

(75) Inventor: Danyu Huang, Shenzhen (CN)

(73) Assignee: Shenzhen Yuantai Medical Equipment Co., Ltd., Shenzhen (CN)

(*) Notice: Subject to any disclaimer, the term of this patent is extended or adjusted under 35 U.S.C. 154(b) by 364 days.

(21) Appl. No.: 13/524,262

(22) Filed: Jun. 15, 2012

(65) Prior Publication Data

US 2013/0048124 A1   Feb. 28, 2013

(30) Foreign Application Priority Data

Aug. 23, 2011   (CN) .......................... 2011 2 0307923

(51) Int. Cl.
  *F16K 15/14*   (2006.01)
  *A61M 39/26*   (2006.01)
  *A61M 16/20*   (2006.01)
  *F16K 27/02*   (2006.01)

(52) U.S. Cl.
  CPC .............. *A61M 39/26* (2013.01); *A61M 16/208* (2013.01); *F16K 27/0209* (2013.01); *A61M 2205/0216* (2013.01); *Y10S 137/903* (2013.01)
  USPC ........... 137/843; 251/356; 137/535; 137/903; 604/99.03; 604/247

(58) Field of Classification Search
  CPC ................. A61M 25/1018; A61M 2039/2486; A61M 2039/2473; A61M 39/24; Y10S 137/903
  USPC ............... 251/356, 149.1; 137/843, 535, 903; 604/920, 99.02–99.03, 247
  See application file for complete search history.

(56) References Cited

U.S. PATENT DOCUMENTS

| | | | | |
|---|---|---|---|---|
| 1,921,761 A | * | 8/1933 | Leins | 251/122 |
| 3,087,492 A | * | 4/1963 | Garth | 604/99.02 |
| 3,192,949 A | * | 7/1965 | De See | 137/540 |
| 3,429,338 A | * | 2/1969 | Bogossian et al. | 137/543.23 |
| 3,831,629 A | * | 8/1974 | Mackal et al. | 137/843 |
| 4,602,655 A | * | 7/1986 | Mackal | 137/515 |
| 4,681,132 A | * | 7/1987 | Lardner | 137/271 |
| 4,776,369 A | * | 10/1988 | Lardner et al. | 137/515.5 |
| 5,284,475 A | * | 2/1994 | Mackal | 604/247 |
| 5,395,348 A | * | 3/1995 | Ryan | 604/247 |
| 2007/0106229 A1 | * | 5/2007 | Wong | 604/249 |

* cited by examiner

*Primary Examiner* — Marina Tietjen
(74) *Attorney, Agent, or Firm* — Garcia-Zamor IP Law; Ruy M. Garcia-Zamor

(57) ABSTRACT

A medical valve having a valve inside housing and a valve core. The valve core is installed within the housing. The housing is preferably an integrally-formed hollow cylindrical structure. An annular protrusion may be arranged on the outer surface of the housing and a seal ring may be arranged in the center of the inner wall of the housing. The valve core can be made of an elastic material as an integrally-formed cylindrical structure. A lock ring matched with the seal ring of the housing may be arranged on the outer surface of the valve core, and the lock ring can be integrally formed with the valve core. The medical valve inside disclosed by the invention is widely applied to the medical fields such as cushion mask, trachea cannula and laryngeal mask, No metal member is preferably employed, so with magnetic resonance imaging examination without causing interference.

9 Claims, 5 Drawing Sheets

MEDICAL VALVE

CROSS REFERENCE TO RELATED APPLICATIONS

This application claims priority to and benefit of Chinese Design Patent Application No. 201120307923.3, filed Aug. 23, 2011, which is hereby incorporated by reference herein as if fully set forth in its entirety.

TECHNICAL FIELD

The invention relates to a valve inside, in particular to a medical valve inside for medical purpose and operation practice.

BACKGROUND ART

Currently, the medical valve inside that is applied widely is typically composed of a housing, a valve core, a lock ring and a spring, wherein the housing is a hollow structure, the valve core is made of a material with quite small rigidity and elasticity and is installed within the housing to be in clearance fit with the housing, and the lock ring and the spring are sleeved outside the valve core and also inside the housing. When in use, a gas injection device is in airtight connection with a gas inlet of the valve inside and pushes the valve core inwards, as a result, the spring is compressed to drive the lock ring to move away from the gas inlet, thus gas can flow in through a clearance between the lock ring and the housing; upon the completion of gas injection, the gas injection device is pulled out and the spring then pushes the valve core to move outwards, as a result, the lock ring returns to the original position to block off the clearance between the valve core and the housing again to achieve the sealing effect.

Such medical valve insides have the defects as follows: 1, interference is liable to occur during magnetic resonance imaging examination owing to the presence of a metal component, i.e. the spring; and 2, the assembly is complex owing to plenty of components, therefore, the production cost is relatively high.

SUMMARY OF THE INVENTION

The objective of the invention is to overcome the shortcomings in the prior art and provide a medical valve inside which is simple in structure, convenient for use, free from the employment of metal members and wider in application.

To achieve the above objective, the technical proposal below is adopted in the invention:

A medical valve inside comprises a valve inside housing and a valve core installed within the housing, and is characterized in that:

(a) the housing is an integrally-formed hollow cylindrical structure, an annular protrusion is arranged on the outer surface of the housing, the part of the housing located at the right side of the annular protrusion is a housing inlet end, the part of the housing located at the left side of the annular protrusion is a housing outlet end, a seal ring is arranged on the inner wall of the housing between the housing inlet end and the housing outlet end, and a valve core fixing structure is arranged at the tail part of the housing outlet end;

(b) the valve core is made of an elastic material and is an integrally-formed cylindrical structure, a lock ring matched with the seal ring of the housing is arranged on the outer surface of the valve core, the part of the valve core located at the right side of the lock ring is a valve core inlet end, the part of the valve core located at the left side of the lock ring is a valve core outlet end; the valve core inlet end passes through the seal ring via the housing outlet end to enter into the housing inlet end, the lock ring of the valve core is in airtight fit with the seal ring of the housing, and the valve core outlet end is fixed in a compression manner by the valve core fixing structure on the housing outlet end.

The valve core is made of an elastic silica gel material.

The right side surface of the lock ring is a conical surface, and the left side surface of the seal ring is a conical surface matched with the conical surface of the lock ring.

The valve core inlet end is a solid cylindrical structure, and a groove is arranged on the right end face of the valve core inlet end.

The valve core inlet end is provided with at least two inlet end reinforcing ribs that are arranged in parallel to the axis of the valve core.

The number of the inlet end reinforcing ribs is six, and the inlet end reinforcing ribs are uniformly distributed along the outer surface of the valve core inlet end.

The valve core outlet end is a hollow cylindrical structure.

The outer surface of the valve core outlet end is provided with at least two outlet end reinforcing ribs that are arranged in parallel to the axis of the valve core.

The number of the outlet end reinforcing ribs is three, and the outlet end reinforcing ribs are uniformly distributed along the outer surface of the valve core outlet end.

The valve core locating structure is a baffler and a locater which are arranged at the tail part of the housing outlet end and which are bent inwards, the baffler and the locater are arranged symmetrically along any diameter of the end face of the housing, and the baffler is clamped by the locator.

When in use, a nozzle of the gas injection device is in airtight connection with the housing inlet end to push the valve core towards the outlet end, the valve core outlet end fails to continue moving leftwards as being blocked by the baffler, and instead, is elastically deformed, the lock ring of the valve core moves away from the inside of the housing, a clearance which is generated between the seal ring and the inner wall of the housing owing to the difference of inner diameters allows for the passage of gas; upon the completion of gas injection, the nozzle of the gas injection device is pulled out, the valve core restores in shape under the action of an own elastic force, the conical surface of the lock ring comes into tight contact with a step inside the housing under the action of the elastic force of the valve core to form an airtight state, therefore, gas leakage can be avoided.

With the above structure, the medical valve inside of the invention can realize the functions of gas passage and sealing, just as the previous medical valve insides; furthermore, the medical valve inside disclosed by the invention is composed of only two members that can be manufactured by means of a method for integral formation, so the medical valve inside has simple structure and convenient manufacturing, and cost can be saved effectually in the case of large-batch production; the two members of the medical valve inside disclosed by the invention are both made of a plastic part, which excludes any metal member from the entire valve inside, therefore, the valve core inside is applicable to devices for a patient who needs magnetic resonance imaging examination, such as cushion mask, trachea cannula and laryngeal mask, in this way, unwanted interference is avoided to result in more precise examination result and wider application.

DETAILED DESCRIPTION OF THE EMBODIMENTS

The invention will be described in further details in conjunction with the accompanying drawings and embodiments.

Figure 1:
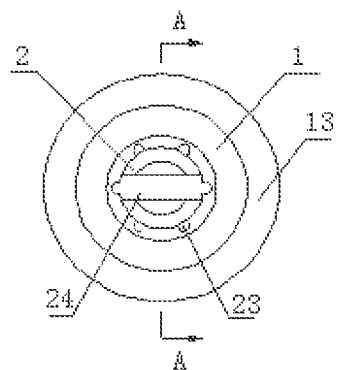
FIG. 1 is a right view of the medical valve inside in the invention.
Figure 2:
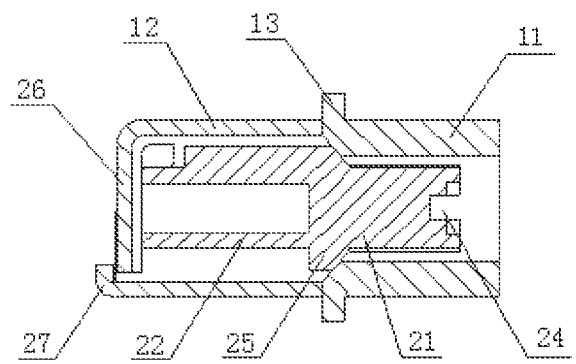
FIG. 2 is a sectional view of FIG. 1 along A-A.
Figure 3:
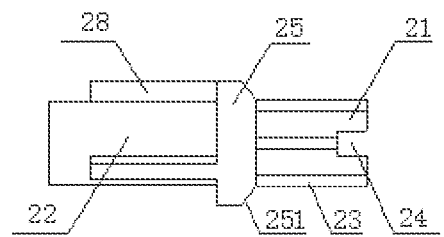
FIG. 3 is a front view of the valve core.
Figure 4:
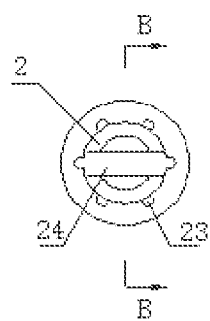
FIG. 4 is a right view of the valve core.
Figure 5:
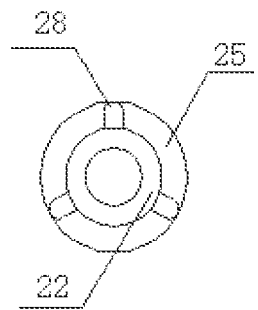
FIG. 5 is a left view of the valve core.
Figure 6:
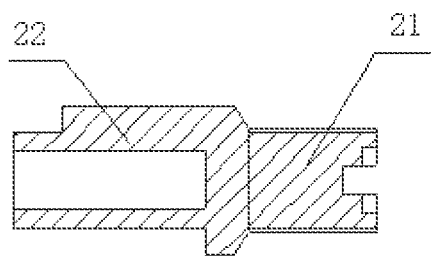
FIG. 6 is a sectional view of FIG. 4 along B-B.
Figure 7:
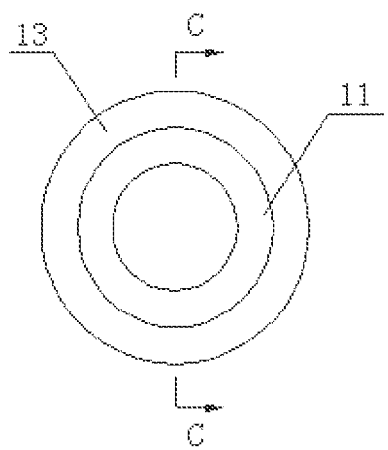
FIG. 7 is a front view of the housing (the locating structure is unbent)
Figure 8:
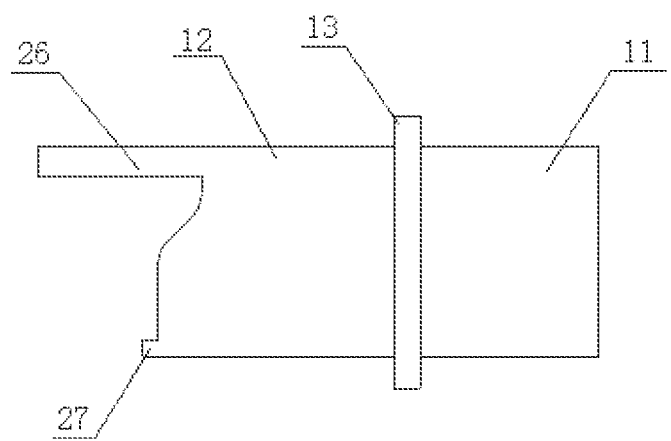
FIG. 8 is a right view of the housing (the locating structure is unbent)
Figure 9:
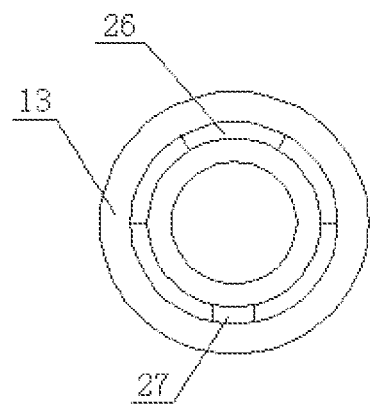
FIG. 9 is a left view of the housing (the locating structure is unbent)
Figure 10:
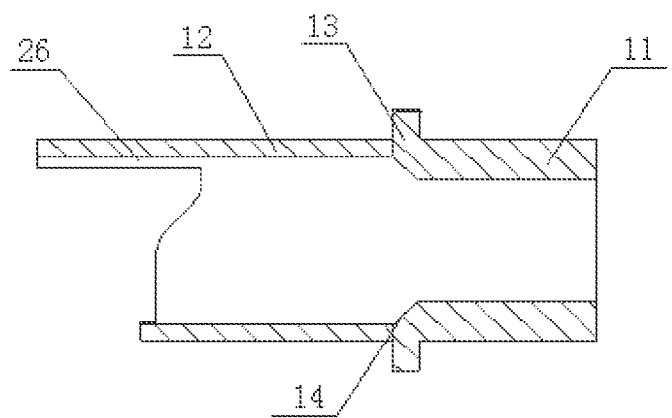
FIG. 10 is a sectional view of FIG. 8 along C-C (the locating structure is unbent).

The medical valve inside, shown as FIG. 1 to FIG. 10, comprises a housing 1 and a valve core 2 installed within the housing 1. The housing 1 is an integrally-formed hollow cylindrical structure, an annular protrusion 13 is arranged on the outer surface of the housing 1, the part of the housing 1 located at the right side of the annular protrusion 13 is a housing inlet end 11, the part of the housing 1 located at the left side of the annular protrusion 13 is a housing outlet end 12, the inner diameter of the housing inlet end is smaller than that of the housing outlet end 12, a seal ring 14 is formed on the inner wall of the housing 1 owing to the difference of the inner diameters of the housing inlet end 11 and the housing outlet end 12, and the left side surface of the seal ring 14 is a conical surface; a baffler 26 and a locater 27 which are bent inwards are arranged at the tail part of the housing outlet end 12, the baffler 26 and the locater 27 are arranged symmetrically along any diameter of the end face of the housing 1, and the baffler 26 is clamped by the locator 27.

The valve core 2 is made of an elastic silica gel material and is an integrally-formed cylindrical structure, a lock ring 25, the right side surface of which is a conical surface 251, is arranged on the outer surface of the valve core 2, the conical surface 251 can be matched with the conical surface of the seal ring 14, the lock ring 25 and the valve core 2 are integrally formed, and the diameter of the lock ring 25 is larger than the inner diameter of the housing inlet end 11. The part of the valve core 2 located at the right side of the lock ring 25 is a valve core inlet end 21 having a solid cylindrical structure, a groove 24 is arranged on the right end face of the valve core inlet end 21, and the valve core inlet end 21 is in clearance fit with the housing inlet end 11; and the part of the valve core 2 located at the left side of the lock ring 25 is a valve core outlet end 22 having a hollow cylindrical structure, and the valve core outlet end 22 is in clearance fit with the housing outlet end 12.

Six inlet end reinforcing ribs 23 are uniformly distributed on the outer surface of the valve core inlet end 21 and are arranged in parallel to the axis of the valve core 2.

Three outlet end reinforcing ribs 28 are uniformly distributed on the outer surface of the valve core outlet end 22 and are arranged in parallel to the axis of the valve core.

When in use, a nozzle of a gas injection device is in airtight connection with the housing inlet end to push the valve core 2 towards the outlet end, the valve core outlet end 22 fails to continue moving leftwards as being blocked by the baffler 26, and instead, is elastically deformed, the lock ring 25 of the valve core moves away from the inside of the housing 1, and a clearance which is generated between the seal ring 14 and the inner wall of the housing 1 owing to the difference of inner diameters allows for the passage of gas; upon the completion of gas injection, the nozzle of the gas injection device is pulled out, the valve core 2 restores in shape under the action of an own elastic force, the conical surface 251 of the lock ring 25 comes into tight contact with a step inside the housing under the action of the elastic force of the valve core to form an airtight state, therefore, gas leakage can be avoided.

The reinforcing ribs in the embodiment can play a role of reinforcing the valve core 2 and stabilizing the movement direction of the valve core 2 while a clearance adequate for the passage of gas is formed, and the groove 24, designed on the end face of the valve core inlet end 21, can effectively avoid the blockage of the nozzle of the gas injection device by the valve core 2, thus avoiding the undesirable outcome of unsmooth gas passage; in addition, the conical surface 251 at the right side of the lock ring 25 is capable of leading to superior contact between the lock ring 25 and the seal ring 14 within the housing 1 under the situation that the valve inside is out of work, accomplishing an excellent airtight effect.

What is claimed is:

1. A medical valve, comprising a housing and a valve core, the valve core being installed within the housing, characterized in that:
   (a) the housing is an integrally-formed hollow cylindrical structure, an annular protrusion is arranged on the outer surface of the housing, a part of the housing located at a right side of the annular protrusion is a housing inlet end, a part of the housing located at a left side of the annular protrusion is a housing outlet end, a seal ring is arranged on the inner wall of the housing between the housing inlet end and the housing outlet end, and a valve core fixing structure is arranged at a tail part of the housing outlet end;
   (b) the valve core is made of an elastic material and is an integrally-formed cylindrical structure, a lock ring matched with the seal ring of the housing is arranged on an outer surface of the valve core, a part of the valve core located at a right side of the lock ring is a valve core inlet end, a part of the valve core located at a left side of the lock ring is a valve core outlet end; the valve core inlet end passes through the seal ring via the housing outlet end to enter into the housing inlet end, the lock ring of the valve core is in airtight fit with the seal ring of the housing, and the valve core outlet end is fixed in a compression manner by the valve core fixing structure on the housing outlet end;
   wherein the valve core fixing structure is a baffler and a locater which are arranged at the tail part of the housing outlet end and which are bent inwards, the baffler and the locater are arranged symmetrically along any diameter of an end face of the housing, and the baffler is clamped by the locator.

2. The medical valve according to claim 1, characterized in that the valve core is made of an elastic silica gel material.

3. The medical valve according to claim 1, characterized in that the right side surface of the lock ring is a conical surface, and the left side surface of the seal ring is a conical surface matched with the conical surface of the lock ring.

4. The medical valve according to claim 1, characterized in that the valve core inlet end is a solid cylindrical structure, and a groove is arranged on a right end face of the valve core inlet end.

5. The medical valve according to claim 4, characterized in that the valve core inlet end is provided with at least two inlet end reinforcing ribs that are arranged in parallel to an axis of the valve core.

6. The medical valve according to claim 5, characterized in that the number of the inlet end reinforcing ribs is six, and the inlet end reinforcing ribs are uniformly distributed along an outer surface of the valve core inlet end.

7. The medical valve according to claim 1, characterized in that the valve core outlet end is a hollow cylindrical structure.

8. The medical valve according to claim 7, characterized in that an outer surface of the valve core outlet end is provided with at least two outlet end reinforcing ribs that are arranged in parallel to an axis of the valve core.

9. The medical valve according to claim 8, characterized in that the number of the outlet end reinforcing ribs is three, and the outlet end reinforcing ribs are uniformly distributed along the outer surface of the valve core outlet end.

\* \* \* \* \*